(12) United States Patent
Zhu et al.

(10) Patent No.: US 9,895,405 B2
(45) Date of Patent: Feb. 20, 2018

(54) USE OF RADIX SALVIAE MILTIORRHIZAE (DANSHEN) OR ITS PREPARATIONS IN PREPARATION OF DRUGS FOR TREATING DISEASES RELATED TO HEPATIC FIBROSIS

(71) Applicant: Tasly Pharmaceutical Group Co., Ltd., Tianjin (CN)

(72) Inventors: Yonghong Zhu, Tianjin (CN); Jinfang Hu, Tianjin (CN); Jie Ma, Tianjin (CN); Xiuping Shen, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 365 days.

(21) Appl. No.: 14/370,711

(22) PCT Filed: Jan. 4, 2013

(86) PCT No.: PCT/CN2013/070037
§ 371 (c)(1),
(2) Date: Jul. 3, 2014

(87) PCT Pub. No.: WO2013/102437
PCT Pub. Date: Jul. 11, 2013

(65) Prior Publication Data
US 2015/0044310 A1     Feb. 12, 2015

(30) Foreign Application Priority Data
Jan. 4, 2012   (CN) .......................... 2012 1 0000557

(51) Int. Cl.
| A61K 36/537 | (2006.01) |
| A61K 36/53 | (2006.01) |
| A61K 36/185 | (2006.01) |
| A61K 31/045 | (2006.01) |
| A61K 9/20 | (2006.01) |
| A61K 9/48 | (2006.01) |

(52) U.S. Cl.
CPC .............. *A61K 36/537* (2013.01); *A61K 9/20* (2013.01); *A61K 9/48* (2013.01); *A61K 31/045* (2013.01)

(58) Field of Classification Search
None
See application file for complete search history.

(56) References Cited

U.S. PATENT DOCUMENTS

2003/0152651 A1    8/2003  Yan et al.
2009/0312413 A1*  12/2009  Song .................... A61K 36/537
                                                       514/468

FOREIGN PATENT DOCUMENTS

| CN | 200410030641.8 | 4/2004 |
| CN | 200410064999.2 | 10/2004 |
| CN | 200610008478.4 | 1/2006 |
| CN | 1759855 A | 4/2006 |
| CN | 200810044624.8 | 6/2008 |
| EP | 1637153 B1 | 3/2009 |
| WO | WO 2011/103789 A1 | 9/2011 |

OTHER PUBLICATIONS (CN 101596202 A, publication date: Dec. 9, 2009).*
Wang et al., "New Developments in Chemistry and Biology of the Bioactive Constituents of Tanshen" Medicinal Research Reviews 27(1):133-148 (2007).
Extended European Search Report, Application No. 13733640.0, dated Feb. 2, 2016.
English Translation of the Abstract of D1 (Progress in Medicine 12, 5, (1992) (pp. 1172-1174).
Wang et al., "Protective Effect of Salvianic Acid a on Acute Liver Injury Induced by Carbon Tetrachloride in Rats", 2007 Pharmaceutical Society of Japan, Bio. Pharm. Bull. 30(1) (pp. 44-47).
Kumazawa et al., "Protective Effects of Various Methanol Extracts of Crude Drugs on Experimental Hepatic Injury Induced by Carbon Tetrachloride in Rats", Pharmaceutical Society of Japan, vol. 110(12), 1990 (pp. 950-957).

* cited by examiner

*Primary Examiner* — Chris R Tate
*Assistant Examiner* — Randall Winston
(74) *Attorney, Agent, or Firm* — Nixon Peabody LLP

(57) ABSTRACT

Present invention relates to a use of Radix Salviae Miltiorrhizae (Danshen) or its preparations in preparation of drugs for treating disease related to hepatic fibrosis.

9 Claims, 3 Drawing Sheets

Control Group

Model Group

FuZhengHuaYu Capsule Group

High-dose Danshen Dripping Pills Group

Middle-dose Danshen Dripping Pills Group

Low-dose Danshen Dripping Pills Group

Normal Group

Model Group

FuZhengHuaYu Capsule Group

High-dose Danshen Dripping Pills Group

Middle-dose Danshen Dripping Pills Group

Low-dose Danshen Dripping Pills Group

Normal Group

Model Group

FuZhengHuaYu Capsule Group

High-dose Danshen Dripping Pills Group

Middle-dose Danshen Dripping Pills Group

Low-dose Danshen Dripping Pills Group

USE OF RADIX SALVIAE MILTIORRHIZAE (DANSHEN) OR ITS PREPARATIONS IN PREPARATION OF DRUGS FOR TREATING DISEASES RELATED TO HEPATIC FIBROSIS

CROSS-REFERENCE TO RELATED APPLICATIONS

This application is an U.S. national stage of PCT/CN2013/070037, filed on Jan. 4, 2013 which claims priority to Chinese Patent Application No. 201210000557.6, filed on Jan. 4, 2012, the contents of which are each incorporated herein by reference in its entirety.

FIELD OF THE INVENTION

The present invention relates to the field of medicine, in particular to a use of Radix Salviae Miltiorrhizae or its preparations in treating diseases related to hepatic fibrosis.

BACKGROUND OF THE INVENTION

Hepatic fibrosis is regarded to be an inevitable stage in liver cirrhosis and therefore anti hepatic fibrosis becomes a very important treating method. Now, the effective anti-hepatic fibrosis medicine is still deficient in clinic. Although several drugs including the cytokines and antioxidant had been studied under clinical research, their clinical efficacy was unsatisfactory. Recently, the traditional Chinese medicine (TCM) has increasingly gained prominence in anti-hepatic fibrosis, showing a promising application prospect.

Radix Salviae Miltiorrhizae (Danshen), bitter in flavor, slightly cold in property, has the therapeutic effectiveness of activating blood by resolving stasis, nourishing blood by tranquilizing mind, cooling blood by removing carbuncle and purging toxin by promoting granulation. It has been regarded as a frequently-used blood-activating and stasis-dissolving medicine. Not only does Danshen contain fat-soluble diterpenoids and water-soluble phenolic acids, but other components, e.g. flavonoids, triterpenes and sterols. Wherein, the diterpenoids with the structure of quinone and ketone include tanshinone I, tanshinone IIA, tanshinone IIR, tanshinone V, tanshinone VI, cryptotanshinone, isotanshinone I, isotanshinone II, isotanshinone IIB and dihydrotanshinone I etc. The water-soluble phenolic acids include Danshensu, protocatechuic aldehyde, protocatechuic acid, caffeic acid and derivatives or depsides condensed with Danshensu and caffeic acid (e.g., salvianolic acid A, salvianolic acid B, salvianolic acid C, salvianolic acid D, salvianolic acid E, salvianolic acid G, Lithospermic acid B, rosmarinic acid and methyl rosmarinate etc.). Aforesaid tanshinone IIA is one of the typical components in the blood-activating and stasis-dissolving diterpenoids. As confirmed by modern pharmacological studies, Danshen has the functions of dilating coronary artery, anti-myocardial ischemia, anticoagulation, anti-formulation of thrombus, sedation, relieving pain, lowering blood lipid and anti-atherosclerosis as well.

In the present invention, hepatic fibrosis model induced with compound factor by $CCl_4$ was established and administrated by i.g. with high, medium and low dosage of the tested drugs of Radix Salviae Miltiorrhizae (RSM) preparations for 7 weeks. Bioactivities of alanine aminotransferase (ALT), aspartate aminotransferase (AST), N-acetyl-β D-glucosaminidase (NAG) and content of total protein (TP), albumin (ALB) and type IV collagen were measured in serum. Bioactivities of superoxide dismutase (SOD), malondialdehyde (MDA), Hyp were measured in liver. Pathomorphological change in liver was observed by HE and Masson staining Expression of α-SMA was measured by immunohistochemistry. As shown in the result, RSM preparations do have the effects of inhibiting the bioactivities of ALT, AST and NGA, lowering the content of type IV collagen in serum, increasing the content of TP and ALB in serum; decreasing the level of Hyp and MDA in liver tissue, increasing the bioactivity of SOD in liver tissue, restricting the growth of collagen fiber in liver tissue as well as reducing expression of α-SMA in liver tissue.

SUMMARY OF THE INVENTION

The objective of the present invention is to provide a use of the RSM or its preparations in the manufacture of medicaments for treating hepatic fibrosis.

Another objective of the present invention is to provide a use of RSM or its preparations in the manufacture of medicaments for treating diseases related to hepatic fibrosis, e.g. liver cirrhosis, hepatitis or liver cancer, etc.

According to the present invention, said RSM may include the fresh RSM medicinal material, the processed RSM medicinal material or a product made from the RSM medicinal material. For example, the RSM is ground or extracted to give a product, in which the extracting method include water-extracting method, ethanol-extracting method or water-extracting and ethanol-precipitating method. Further, refining steps, e.g. resin purification, may be included.

According to the present invention, said RSM preparations include the medicine which is made from the RSM medicinal material. By now, said RSM preparations which are already commercially available include Salvia Tablets, Salvia Capsules and Salvia dripping pills.

According to the present invention, said RSM preparations are prepared by a method comprising following steps: firstly the medicinal materials are processed to give bioactive components which are further made into the preparations.

According to the present invention, the preparing methods of the RSM preparations belong to the prior art, which can be obtained from the publication of Chinese patent or the published drug standard.

According to the present invention, said RSM preparation is preferably selected from the RSM dripping pills.

According to the present invention, said RSM preparation is a pharmaceutical composition made from the RSM. Said composition comprises 0.1-99.9 wt % of pharmaceutically acceptable carriers. Said pharmaceutical composition is prepared in the form of unit dosage and said unit dosage refers to individual preparation, e.g. each tablet of tablets, each capsule of capsules, each bottle of oral solutions, each bag of granules and each injection of injections.

According to the present invention, said RSM preparations can be prepared in any pharmaceutically acceptable dosage form, including the tablet such as sugar-coated tablet, film-coated tablet and enteric-coated tablet, the capsule such as soft capsule and hard capsule, the oral liquid solution, the buccal tablet, the granules, the instant powder, the pill, the pulvis, the paste such as ointment and paster, the Dan, the suspension, the powder, the solution such as injection, the suppository, the cream, the spray, the drop, the dipping pill and the patch.

According to the present invention, said orally-administrated dosage form can include commonly-used excipients such as the adhesive, filling agent, diluent, tableting agent, lubricant, disintegrating agent, colorant agent, flavoring agent, wetting agent. If necessary, the tablet may be coated.

According to the present invention, suitable filling agents include cellulose, mannitol, lactose and other analogous filling agents. Suitable disintegrating agents include starch, polyvinylpyrrolidone (PVP) and starch derivative (i.e. sodium hydroxyethyl starch). Suitable lubricants include magnesium stearate. Suitable wetting agents which are pharmaceutically acceptable include sodium dodecyl sulfate.

According to the present invention, oral solid preparations of said composition can be prepared by commonly-used methods, e.g., blending, filling and tableting. By blending repeatedly, one can make the bio-active components (API) distributed uniformly into a large amount of filling agent.

According to the present invention, oral liquid preparations are in dosage form of either water-soluble or oil-soluble suspension, solution, emulsion, syrup or elixir, or drying powder that is always reconstituted with water or other suitable solvents before clinical use. This liquid preparation may contain conventional additives, for example: suspending agent, e.g. sorbitol, syrup, methylcellulose, gelatin, hydroxy ethyl cellulose, hydroxy methyl cellulose, aluminum stearate gel or hydrogenated edible fat; emulsifying-agent, e.g. lecithin, sorbitan monoleate or arabic gum; non-aqueous carriers (including edible oil) e.g. almond oil, fractionated coconut oil, oil ester (such as glyceride), propylene glycol or ethanol; as well as preservative e.g. methylparaben, nipasol, sorbic acid. If necessary, conventional flavoring agents or colorant agents can be included.

According to the present invention, said injection contains bio-active components and aseptic carriers. Said bio-active components can be dissolved or suspended depending on the type and concentration of carriers. Generally, a solution is prepared by dissolving the bio-active component in the carrier, sterilizing, loading into a suitable vial or ampoule and sealing. Some adjuvants, e.g. local anaesthetic, preservative and buffering agent can be dissolved in the carrier. In order to improve its stability, after being loaded into the vial, this composition of the present invention can be froze and dried in vacuum to remove water.

According to the present invention, said RSM preparation can be prepared by optionally adding pharmaceutically acceptable carriers. Said carriers include but are not limited to the substances selected from: sugar alcohol, e.g. mannitol, sorbitol, xylitol; amino acid, e.g. cysteine hydrochloride, methionine, glycine; Vitamin C; EDTA disodium, EDTA calcium disodium salt; inorganic salt, e.g. one valence alkali carbonate, acetate, phosphate or its aqueous solution, sodium chloride, potassium chloride, sodium pyrosulfite, sodium bisulfite, sodium thiosulfate; calcium carbonate, calcium bicarbonate; stearate, e.g. calcium stearate, magnesium stearate; inorganic acid, e.g. hydrochloride, sulfate, phosphoric acid; organic acid, e.g. acetic acid, mercaptoacetic acid; organic acid salt, e.g. sodium lactate; oligosaccharide, polysaccharide, cellulose and its derivatives, e.g. maltose, glucose, fructose, dextran, sucrose, lactose, cyclodextrin (β-cyclodextrin), starch; silicon derivative; alginate; gelatin; PVP; glycerol; Tween-80, agar gel; surfactant; polyethylene glycol (PEG); phospholipids; Kaolin; talcum powder etc.

According to the present invention, protocol and dosage of said RSM preparation depends on the condition of patients in clinic. For example, the RSM dripping pills prepared by the method of EXAMPLE 1 are administrated to patient, with 20 pills each time and 3 times daily, 24-32 weeks as a course of treatment.

EXAMPLES

Figure 1:
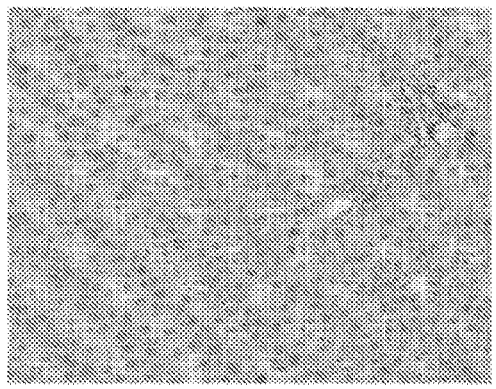
FIG. 1 illustrates the influence of α-SMA expression by the RSM dripping pills in $CCl_4$-induced hepatic fibrosis in rats (10×20).
Figure 1:
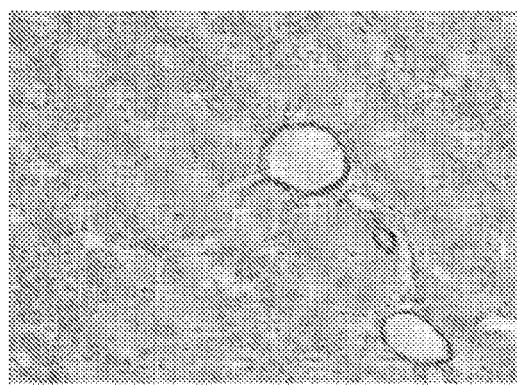
Figure 1:
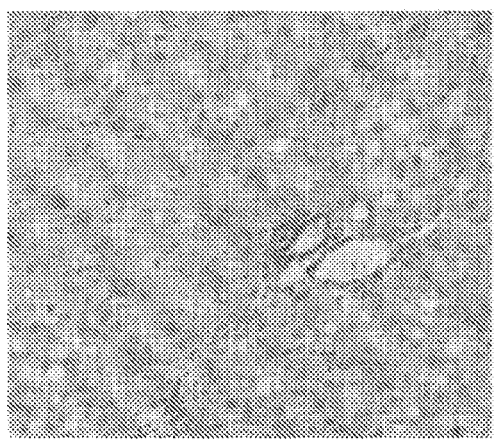
Figure 1:
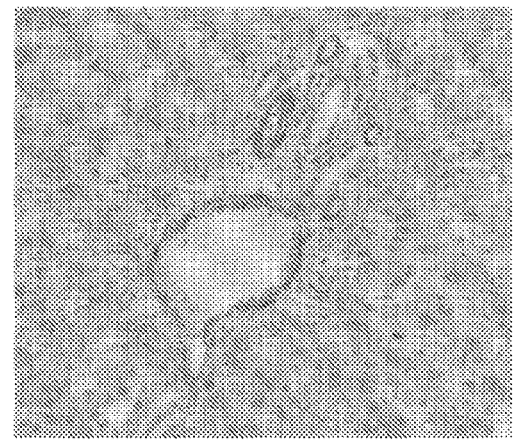
Figure 1:
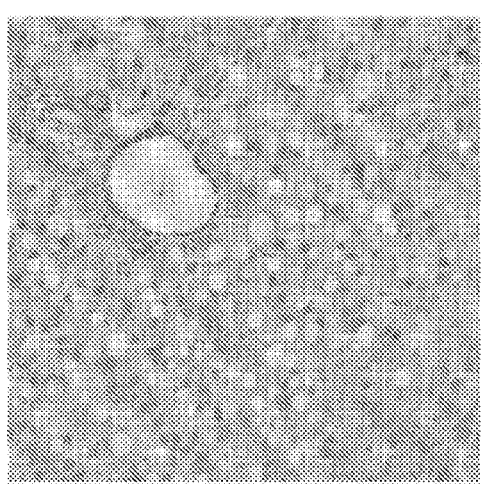
Figure 1:

The following examples are offered for purposes of illustration only and do not intend to limit the scope of the invention in any way.

Example 1 Preparation of the RSM Dripping Pill

Formulation:
Radix Salviae Miltiorrhizae 100 g was used to give 1000 pills.
Preparing Method:
Coarsely-ground Radix salvia Miltiorrhizae was placed into an extraction tank, into which water with 7 times the weight of the Radix salvia Miltiorrhizae crude medicine was poured to decoct for 2 times, 2 hours each time. After combination of the decoction, the solution was filtered and concentrated until the volume-to-weight ratio was 1 L:1 kg to obtain an extract. The supernatant of the extract was collected by centrifugation and passed through the macroporous resin. The resin was washed with water, eluted with ethanol and the eluent was concentrated to give the RSM extract with the relative density of 1.31~1.38 (50-60° C.) and concentration of no less than 10 mg Danshensu in 1 gram of extract. Aforesaid RSM extract was added with a proper amount of PEG, stirred well, melted on a water bath and transferred into the tank of dripping machine. Temperature was kept at 75~85° C. A Suitable dripper was selected in light of the weight of pill. Aforesaid RSM extract was dropped into the ice-bath cooled liquid paraffin with a speed of 60-80 pills per minute. After being formed, the pills were taken out and cleaned with blotting paper to remove the surface liquid paraffin. The product was given.

Example 2 Preparation of RSM Tablet

Formulation:
RSM extract 262 g, starch 40 g, light magnesium oxide 60 g, magnesium stearate 7 g, talcum powder 80 g to prepare 1000 tablets
Preparing Method:
Coarsely-ground Radix salvia Miltiorrhizae was extracted with 95% ethanol for 3 times, 2 hours each time. After ethanol recovery, the extract was concentrated to give a thick extract. Resulting drug residue was decocted with water for 2 times, 1 hour for each time, and further filtered. The filtrate was concentrated to a proper volume and blended with aforesaid thick extract to have the RSM extract.

Aforesaid RSM extract was heated (without direct flame) to 60° C.-70° C., melted by stirring, added with the light magnesium oxide, talcum powder (60 g) and starch respectively, blended well and placed on a drying plate. The resulting materials were dried under 60° C. to moisture content of no more than 3% and ground into granules (blocks) under mesh 14. Finally, the magnesium stearate and talcum powder (20 g) were added, well blended to granulate with 12 mesh sieve, tableted, checked and coated with sugar.

Example 3 Preparation of RSM Capsule

Formulation:
RSM extract 406 g, starch 40 g, and 10% starch slurry to prepare 1000 capsules
Preparing Method:
Coarsely-ground Radix salvia Miltiorrhizae was extracted with 95% ethanol for 3 times, 2 hours each time. After ethanol recovery, the extract was concentrated to give a thick extract. Resulting drug residue was decocted with water for 2 times, 1 hour for each time, and further filtered. The filtrate was concentrated to a proper volume and blended with aforesaid thick extract to have the RSM extract.

Aforesaid RSM extract was pulverized and passed 80 mesh sieve and added with 10% starch slurry to make soft material to granulate by 14 mesh nylon sieve. The resulting granules were dried at 70° C. to the moisture content of no more than 3%. These granules were blended and loaded into #1 capsule shell to give the product.

Example 4 Preparation of RSM Granule

Formulation:
RSM 100 g to prepare 1000 granules
Preparing Method:
Coarsely-ground Radix salvia Miltiorrhizae was placed into an extraction tank, into which water with 7 times the weight of the Radix salvia Miltiorrhizae crude medicine was poured to decoct for 2 times, 2 hours each time. After combination of the decoction, the solution was filtered and concentrated until the volume-to-weight ratio was 1 L:1 kg to obtain an extract. The supernatant of the extract was collected by centrifugation and passed through the macroporous resin. The resin was washed with water, eluted with ethanol and the eluent was concentrated to give the RSM extract with the relative density of 1.31~1.38 (50-60° C.) and concentration of no less than 10 mg Danshensu in 1 gram of extract. Aforesaid RSM extract was added with 5 times of sugar powder, blended well, added with 70% ethanol to make a soft material. Aforesaid soft material was granulated by 14 mesh nylon sieve. The resulting wet granules were dried at 60° C. The dried granules were sieved firstly by 14 mesh sieve and by No. 4 sieve (65 mesh) to get rid of the fine powder, loaded separately, sealed to give the product.

Trial Example 5: Efficacy Study of RSM Preparations

Activation of the HSC (hepatic stellate cell) and extracellular matrix (ECM) overdeposition are both believed to be the crucial events to hepatic fibrosis. Always, the activated HSC is proliferated, and converted into myofibroblast to generate a large amount of ECM. $CCl_4$-induced hepatic fibrosis was used in this experiment, because its mechanism lies in that it can directly hydrolyze membrane of liver cell, leading to liver cell degenerative necrosis. Toxicity of $CCl_4$ is mainly related to its active metabolite. $CCl_4$ is metabolized into active chloroform free radicals and chloride radicals by mixed function oxidase in liver cells. These free radicals can finally make enzyme of the liver cell lose function, membrane lipid peroxidation and concentration of calcium increased, causing liver cell injured necrosis and fibrosis. This fibrosis model, however, has self-cure tendency. So the research was carried out in a manner of preventive administration. Activities of ALT and AST are sensitive biomarker for injury of liver cells. Reduction of TP and ALB is in proportion to the injury of synthetic function in liver cell.

One of the key factors of hepatic fibrosis is ECM overdeposition. Collagen is the main constituent of ECM and Hyp is the main constituent of collagen. Hyp of liver cell, changing with the decrease/increase of collagen during the progress of fibrosis, is identified as the important marker for evaluation of collagen content and degree of liver fibrosis. NAG, a proteolytic enzyme of lysosome, takes part in hydrolytic metabolism of connective tissue matrix. Its activity in serum is thought to be correlated with the hepatic fibrosis, revealing connective-tissue-collagen decomposition. Similarly, the change of content of type IV collagen in serum is confirmed to be an extremely practical marker to judge degree of hepatic fibrosis.

Under normal conditions, HSC remains in stationary state. Under pathological conditions, HSC is activated, and expresses α-SMA (α-smooth muscle actin). The SMA expressed by HSC is seen as one of its significant characteristics. Immunohistochemical technique and image analysis software were used to analyze α-SMA to show the effect of medicine.

On the basis of aforesaid factors, a pharmacological experiment for the RSM preparations had been designed as follows:
1. Material
1.1 Animals
Wistar male rats, weighing 140-160 g, were purchased from Tianjin Shanchuanhong Animal Co., Ltd. (Certification number: SCXK (JIN) 2009-0001).
1.2 Reagents
ALT, AST, TP and ALB kits were obtained from BioSino Bio-technology and Science Inc. SOD, MDA, Hyp and NGA kits were purchased from Nanjing Jiancheng Biochemical Institute. Type IV collagen kit was purchased from Adlitteram diagnostic laboratories Inc. α-SMA mouse monoclonal antibodies were obtained from abcam Inc. Monoclonal antibody kit, DAB coloring kit were purchased from Beijing Zhongshanjinqiao Inc. $CCl_4$ was purchased from Tianjin Tianhe Reagent Factory. Fuzhenghuayu (FZHY) capsule (Batch No.: 100403) was purchased from Shanghai Huanghai Pharmaceutical Company, and resolved with distilled water to prepare suspension before use. The RSM dripping pill (Batch No.: 100101) was produced by Tianjin Tasly Pharmaceutical Co., Ltd in accordance with the method of EXAMPLE 1.
1.3 Apparatus
LXJ-IIB low-speed large-capacity multi-tube centrifuge was purchased from Shanghai Anting Apparatus Inc. SUNRISE enzyme mark instrument was produced by SUNRISE Austria. PL 203 electronic balance was produced by METTLER TOLEDO (Shanghai) Inc. Hitachi 7080 auto chemistry analyzer was produced by Hitachi Inc Japan. Olympus BH-2 ordinary microscope was purchased from Olympus Inc Japan.
2. Method
2.1 Establishment of Model
Except the control group, the rats in other groups were injected subcutaneously (sc) with pure $CCl_4$ at 5 ml/kg for the first time and then with 40% sc pure $CCl_4$-olive oil at 3 ml/kg every 3 days for 7 weeks. During first 2 weeks, the rats were fed with diet of 20% pig oil and 0.5% cholesterol and simple corn meat diet during $3^{rd}$ to $6^{th}$ week.

2.2 Grouping and Administration 90 healthy male rats, weighing 140 g~160 g, were randomly divided into 6 groups: control group (n=10), model group (n=16), FZHY group (1500 mg/kg, n=16), RSM dripping pill high-dose (700 mg/kg), medium-dosage (350 mg/kg) and low-dosage (175 mg/kg) groups (n=16). The rats were administrated with corresponding medicines by i.g. at the day of making model and with distilled water (10 mL/kg) to the control and model group for 7 weeks. 1 hour after last administration, the rats were anesthetized by intramuscular injection of pentobarbital sodium to draw blood from abdominal aorta. Serum was collected by centrifuge for later use. Hepatic tissue at same position was quickly taken out, fixed in 12% formalin liquid for HE staining and Masson staining Hepatic tissue in other position was fixed in 10% formalin liquid for immunohistochemical staining and the rest of hepatic tissue was prepared into 10% liver tissue homogenate by normal saline.

2.3 Measurement of Biomarker

Biomarkers were measured, e.g. activity of ALT, AST, content of TP, ALB, NAG and type IV collagen, activity of hepatic SOD and content of MDA and Hyp, expression of α-SMA by immunohistochemical staining, HE staining and Masson Staining after paraffin section.

2.4 Expression of α-SMA in Hepatic Tissue Measured by Immunohistochemical Method The paraffin sections were deparaffinized by normal method, hydrated and washed with PBS for 15 min. Intrinsic peroxidase was closed with 3% $H_2O_2$, incubated at room temperature for 10 min and washed with PBS for 15 min. Further, they were placed 0.01 mol/L sodiocitrate buffering solution to repair for 15 min on electrical magnetism stove, washed for 15 min with PBS after self cooling and unnecessary solution was removed. α-SMA monoclonal antibody (1:100) was dripped, incubated at 37° C. for 1 hour and washed with PBS for 15 min. Polymer Helper was dripped, incubated at 37° C. for 20 min, and washed with PBS for 15 min. Poly-HRP anti-Mouse IgG monoclonal antibody was dripped, incubated at 37° C. for 20 min, washed with PBS for 15 min, colored by DAB, washed with tap water for 10 min, re-stained by hematoxylin, dehydrated, cleared and sealed for microscopic examination. The α-SMA staining was brownish yellow. The image was analyzed with image analysis software (Image-Proplus 6.0) and 5 fields of vision were selected randomly to record integral optical density (IOD). The more IOD value is, the stronger positive expressive products are.

2.5 Histopathological Examination

After HE staining and Masson staining, the degree of liver fibrosis was examined under microscope and analyzed semi-quantitatively. Grading standards of hepatic fibrosis were present as follows:

"−" represented normal liver, in which extremely few fibrous connective tissue was observed in portal area, which is in a normal state;

"+" represented collagen proliferation in portal area and around central vein in hepatic lobule, where few fibrosis bundle spread and irradiation in central vein and portal vein was observed without formation of fibrous septa and hepatic lobules remained unchanged;

"++" represented collagen proliferation, where fibrosis bundle spread and irradiation in central vein and portal vein was observed with formation of incomplete interval, and hepatic lobules reserved mostly;

"+++" represented mass collagen proliferation, where small amount of false lobe was formed with destruction of the lobular structure;

"++++" represented thickened septal and false lobe was formed.

2.6 Statistical Analysis

SPSS11.5 software package was used to analyze data and t-test was used to analyze the inter-group difference. Data were expressed as $\bar{x}\pm s$. Lesion degree of pathological tissues was analyzed with SPSS11.5 NPar Tests Mann-Whitney Test and illustrated by Excel.

3. Results 3.1 Effect on serum ALS, AST, TP and ALB of Hepatic Fibrosis Rats

As shown in Table 1, compared with the control group, the activity of serum ALT and AST was increased significantly (P<0.01) and the content of TP and ALB reduced significantly (P<0.01). Compared with the model group, the content of TP and ALB in the RSM dripping pill groups of medium and low dosage was increased significantly (P<0.05) and the activity of serum ALT and AST reduced significantly (P<0.05).

3.2 Effect on Serum NGA and Type IV Collagen of Hepatic Fibrosis Rats

As shown in Table 2, compared with the control group, the activity of serum NGA was increased significantly (P<0.01) and type IV collagen increased. Compared with the model group, activity of serum NGA in the RSM dripping pill groups of 3 dosages was reduced significantly (P<0.01) and content of type IV collagen in the RSM dripping pill medium-dosage and low-dosage groups was reduced (P<0.05).

3.3 Effect on Activity of SOD and Level of MDA and Hyp in Liver Tissue of Hepatic Fibrosis Rats As shown in Table 3, compared with the control group, activity of SOD in liver tissue of model rats was reduced significantly (P<0.05), and level of MDA and Hyp was increased significantly (P<0.01). Compared with the model group, activity of SOD in the RSM dripping pill groups of 3 dosages was increased significantly (P<0.05), the level of MDA in the RSM dripping pill low-dosage group reduced significantly (P<0.05) and level of Hyp in the RSM dripping pill groups of 3 dosages reduced significantly (P<0.01).

3.4 Effect on Expression of α-SMA in Liver Tissue of Hepatic Fibrosis Rats

As shown in FIG. 1 and Table 4, positive staining in the control group was found in vessel wall. Compared with the control group, the positive expression of α-SMA in the model group was strengthened clearly. Positive staining was widely expressed in the fibrous septa, vessel wall and fibrous tissue proliferation area. There was no expression in biliary tract cell. Distribution of α-SMA positive expression in the RSM dripping pill groups of 3 dosages was similar with the ones in the model group, but yellow sclera area was somewhat reduced. By IOD examination, compared with the control group, the IOD value in was increased significantly (P<0.05). Compared with the model group, the IOD values in the RSM dripping pill groups of medium and low dosages were reduced significantly (P<0.05). As shown in the results, the RSM dripping pills can resist the enhancement of the α-SMA expression and inhibit HSC proliferation in liver tissue of hepatic fibrosis rats.

3.5 Effect on Pathologic Morphology in Liver Tissue of Hepatic Fibrosis Rats

Figure 2:
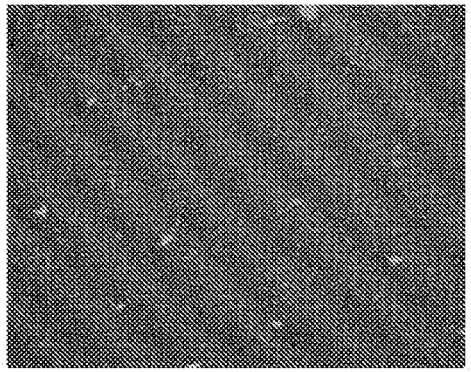
FIG. 2 illustrates the influence of pathologic morphology by the RSM dripping pills in $CCl_4$-induced hepatic fibrosis in rats (HE straining, 10×10).
Figure 2:
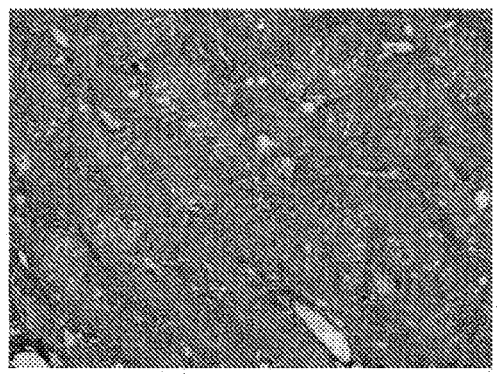
Figure 2:
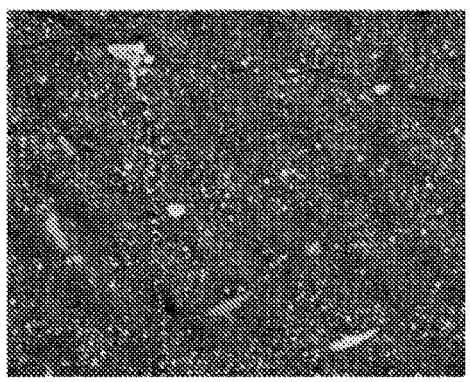
Figure 2:
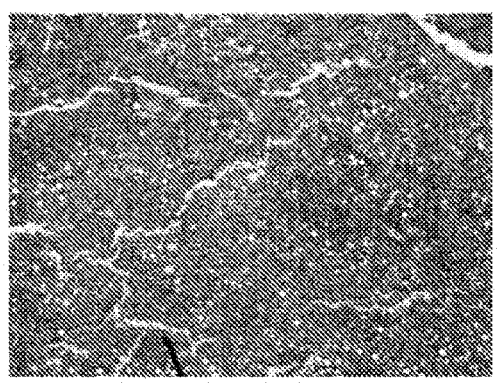
Figure 2:
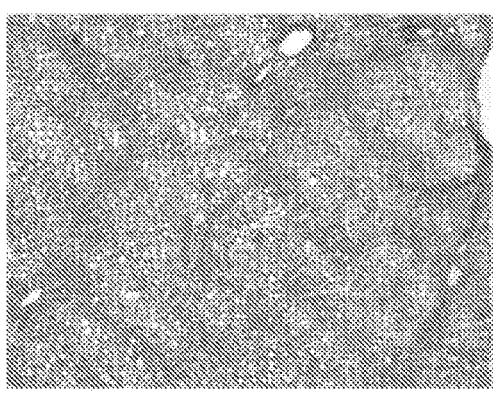
Figure 2:
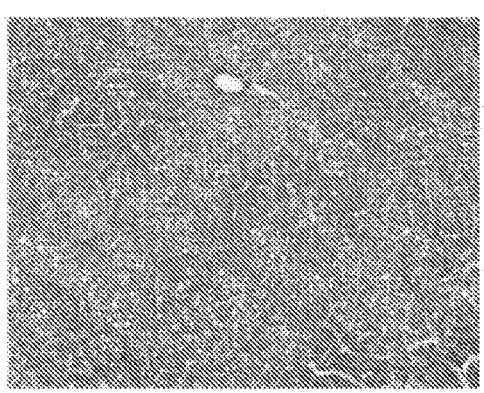
Figure 3:
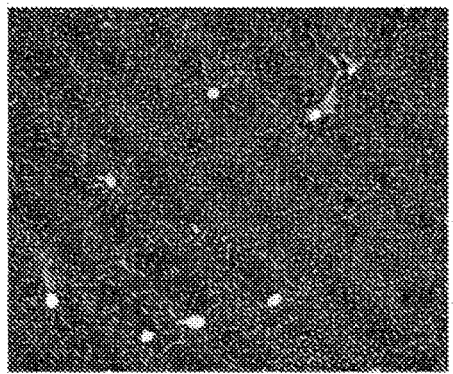
FIG. 3 illustrates the influence of pathologic morphology by the RSM dripping pills in $CCl_4$-induced hepatic fibrosis in rats (Masson straining, 10×10).
Figure 3:
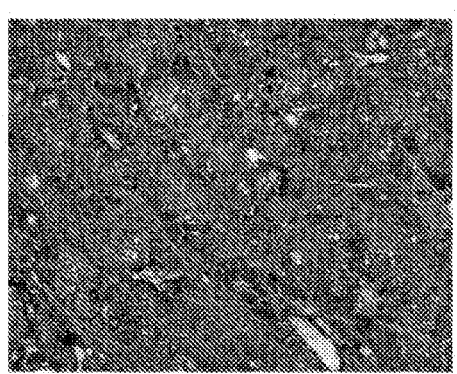
Figure 3:
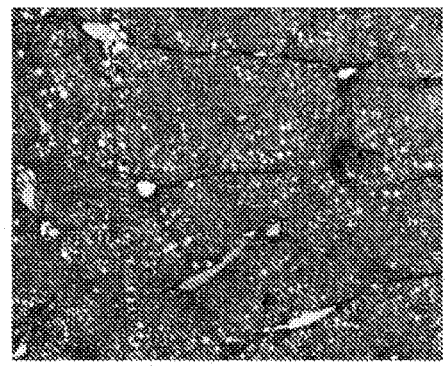
Figure 3:
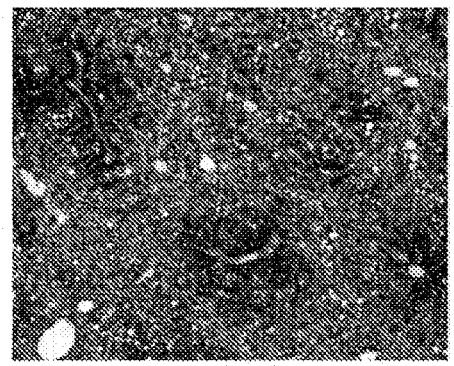
Figure 3:
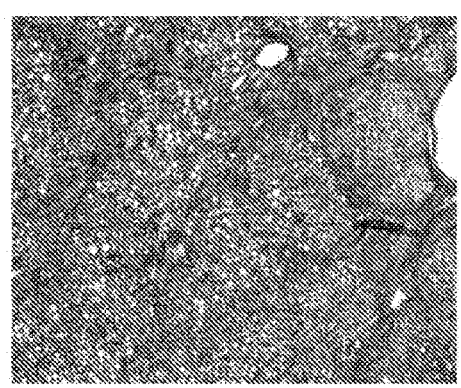
Figure 3:
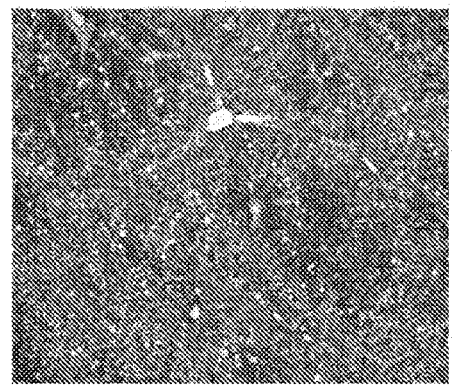

As shown in Table 5, FIG. 2 and FIG. 3, it was found that the hepatic lobule in control group was integral, tissue was clear, liver cells were morphologically normally arranged in cords centered by central vein and liver sinus was clear. There were extremely few fibrosis tissues in a bigger portal area, which is in a normal state. Compared with the control group, hepatic lobules in rats of the model group were damaged at different levels, hepatic cells arranged in disorder, fibrosis tissues proliferated at different levels in portal area, central vein and portal vein, indicating successful modeling. Aforesaid diseases were found in rats of administration groups, significantly less than that of the model group. Fibrosis of rats was graded in light of pathological change and grading standard of fibrosis at home and abroad. Significance test was for grading result. The RSM dripping pills of 3 dosages can improve the hepatic fibrosis markedly ($P<0.05$, $P<0.01$). As shown in the results, the RSM has significantly protective effect on hepatic fibrosis rats.

TABLE 1

Effect of RSM dripping pills on serum ALS, AST, TP and ALB in $CCl_4$-induced hepatic fibrosis rats $\bar{x} \pm s$)

| Groups | n | dosage (mg · kg$^{-1}$) | ALT (U · L$^{-1}$) | AST (U · L$^{-1}$) | ALB (g · L$^{-1}$) | TP (g · L$^{-1}$) |
|---|---|---|---|---|---|---|
| Control group | 10 | — | 35.49 ± 6.99 | 160.90 ± 21.85 | 33.4 ± 1.0 | 59.06 ± 2.59 |
| Model group | 9 | — | 98.17 ± 55.38$^{ΔΔ}$ | 232.99 ± 96.09 | 27.74 ± 3.76$^{ΔΔ}$ | 47.93 ± 4.75$^{ΔΔ}$ |
| FZHY capsule | 10 | 1500 | 34.35 ± 3.51** | 152.62 ± 12.02* | 29.91 ± 1.12 | 50.66 ± 2.14 |
| RSM | 9 | 700 | 69.06 ± 25.62 | 179.38 ± 25.06 | 30.11 ± 2.13 | 51.86 ± 3.39 |
| RSM | 10 | 350 | 40.85 ± 12.49* | 154.50 ± 23.21* | 31.33 ± 1.45* | 53.68 ± 3.37* |
| RSM | 9 | 175 | 46.74 ± 11.75* | 170.19 ± 26.27 | 31.44 ± 1.14* | 52.79 ± 1.72* |

Compared with the control group,
$^{ΔΔ}P < 0.01$; compared with the model group,
*$P < 0.05$,
**$P < 0.01$

TABLE 2

Effect on serum NGA and type IV collagen in $CCl_4$-induced hepatic fibrosis rats ($\bar{x} \pm s$)

| Groups | N | Dosage (mg · kg$^{-1}$) | NAG (U · L$^{-1}$) | Type IV collagen (ng · ml$^{-1}$) |
|---|---|---|---|---|
| Control group | 10 | — | 24.87 ± 8.20 | 0.64 ± 0.16 |
| Model group | 9 | — | 38.45 ± 7.53$^{ΔΔ}$ | 1.04 ± 0.70 |
| FZHY capsule | 10 | 1500 | 21.27 ± 10.15** | 0.55 ± 0.23 |
| RSM | 9 | 700 | 28.32 ± 6.56** | 0.89 ± 0.47 |
| RSM | 10 | 350 | 25.90 ± 8.78** | 0.49 ± 0.19* |
| RSM | 9 | 175 | 28.23 ± 5.47** | 0.46 ± 0.06* |

Compared with the control group,
$^{ΔΔ}P < 0.01$; compared with the model group,
*$P < 0.05$,
**$P < 0.01$

TABLE 3

Effect on activity of SOD and level of MDA and Hyp in liver tissue of $CCl_4$-induced hepatic fibrosis rats ($\bar{x} \pm s$)

| Groups | n | Dosage (mg · kg$^{-1}$) | SOD (U · ml$^{-1}$) | MDA (nmol · mgprot$^{-1}$) | Hyp (μg · (g of liver)$^{-1}$) |
|---|---|---|---|---|---|
| Control groups | 10 | — | 63.01 ± 14.22 | 1.21 ± 0.29 | 127.89 ± 13.68 |
| Model groups | 9 | — | 46.06 ± 13.31$^{Δ}$ | 5.18 ± 2.70$^{ΔΔ}$ | 242.11 ± 56.13$^{ΔΔ}$ |
| FZHY capsule | 10 | 1500 | 54.77 ± 8.28 | 4.12 ± 2.27 | 165.26 ± 38.81** |
| RSM | 9 | 700 | 58.01 ± 9.34* | 3.73 ± 1.49 | 177.58 ± 56.82* |
| RSM | 10 | 350 | 58.41 ± 11.12* | 3.87 ± 2.47* | 176.49 ± 34.89* |
| RSM | 9 | 175 | 58.46 ± 5.70* | 2.22 ± 0.51 | 157.12 ± 31.11* |

Compared with the control group,
$^{Δ}P < 0.05$,
$^{ΔΔ}P < 0.01$; compared with the model group,
*$P < 0.05$,
**$P < 0.01$

TABLE 4

Effect on expression of α-SMA in liver tissue of CCl$_4$-induced hepatic fibrosis rats ($\bar{x} \pm s$)

| Groups | n | Dosage (mg · kg$^{-1}$) | IOD(×10$^2$) |
|---|---|---|---|
| Control groups | 10 | — | 5.08 ± 0.81 |
| Model groups | 9 | — | 20.54 ± 6.71$^\Delta$ |
| FZHY capsule | 10 | 1500 | 9.62 ± 3.53* |
| RSM | 9 | 700 | 12.12 ± 2.92 |
| RSM | 10 | 350 | 9.75 ± 1.68* |
| RSM | 9 | 175 | 8.39 ± 1.25* |

Compared with the control group,
$^\Delta$P < 0.05; compared with model group,
*P < 0.05,
**P < 0.01

TABLE 5

Effect on pathologic morphology in liver tissue of CCl$_4$-induced hepatic fibrosis rats

| Groups | n | Degree of hepatic fibrosis | | | | | P value |
|---|---|---|---|---|---|---|---|
| | | − | + | ++ | +++ | ++++ | |
| Control group | 10 | 10 | 0 | 0 | 0 | 0 | .0000 |
| Model group | 9 | 0 | 0 | 1 | 7 | 1 | — |
| FZHY capsule | 10 | 0 | 3 | 3 | 3 | 1 | 0.056 |
| RSM high dosage group | 9 | 0 | 2 | 4 | 2 | 1 | 0.045 |
| RSM medium dosage group | 10 | 0 | 2 | 5 | 2 | 1 | 0.028 |
| RSM low dosage group | 9 | 0 | 4 | 5 | 0 | 0 | 0.000 |

Compared with the model group,
*P < 0.05,
**P < 0.01

As shown in the results, the RSM dripping pills can significantly inhibit the increase of ALT and AST and enhance synthesis of TP and ALB, especially for the medium and low dosages. It is shown that the RSM dripping pills have the effect of protecting liver cell and inhibiting liver damage.

As shown in the results, the RSM dripping pills can inhibit the increase of Hyp and type IV collagen and reduce the activity of NAG, especially for the medium and low dosages. It is shown that the RSM dripping pills have the effect of inhibiting precipitation of collagen by promoting degradation of collagen, significantly improving the degree of hepatic fibrosis. Change of SOD and MDA displays the degree of liver damage directly or indirectly. As shown in the results, the RSM dripping pills can increase the activity of SOD, lowering the level of MDA, especially for the medium and low dosages. It is indicated that the RSM dripping pills have the effect of lowering free radical and reducing lipid peroxidation.

As shown in the results, the RSM dripping pills can inhibit higher expression of α-SMA, especially for medium and low dosages. It is shown that the RSM dripping pills have effect of inhibiting HSC proliferation. Its mechanism of anti-fibrosis has the relationship with inhibiting expression of α-SMA by HSC. As shown in the results of pathological examination, the RSM dripping pills can significantly improve damage caused by hepatic fibrosis, especially for the and low dosages, indicating the protective effect on hepatic fibrosis rats.

REFERENCE

[1] Adrian J E, Poelstra K, Scherphof G L, et al. Effects of a new bioactive lipid-based drug carrier on cultured hepatic stellate cells and liver fibrosis in bile duct-ligated rats [J]. J Pharmacol Exp Ther, 2007, 321(2):536-543.

[2] Prud home G J. Pathobiology of transforming growth factor beta in cancer, fibrosis and immunologic disease, and therapeutic consideration [J]. Lab Invest, 2007, 87(11):1077-1091.

[3] Song M, Song Z, Barve S, et al. Tetrathiomolybdate protects against bile duct ligation-induced cholestatic liver injury and fibrosis [J]. J Pharmacol Exp Ther, 2008, 325(2):409-416.

[4] Miao X D, Yan J, Ying B Z, et al. Emodin protects rat liver from CCL4-induced fibrogenesis via inhibition of hepatic stellate cells activation [J]. World J Gastroenterol, 2009, 15(38):4753-4762.

[5] ZOU Y H, Yang Y, Li J, Wu Q, et al. Potential therapeutic effects of a traditional Chinese formulation, BJ-JN, on liver fibrosis induced by carbon tetrachloride in rats [J]. J Ethnopharmacol, 2008, 120(3):452-457.

[6] Yuan L P, Chen F H, Ling L, et al. Protective effects of total flavonoids of *Bidens bipinnata* L. against carbon tetrachloride-induced liver fibrosis in rats [J]. J Pharm Pharmacol, 2008, 60(10):1393-1402.

[7] Qin Y, Yan L, Tang L, et al. Effect of tanshinone IIA on collagen expression in liver tissue of hepatic fibrosis ras [J]. Lishizhen Medicine and Materia Medica Research, 2010, 21(4): 782-784.

[8] Chen H, Zhang J H, Liu W Q, Effect of curcumin for anti-schistosomiasis hepatic fibrosis and the experimental study of its mechanism [J]. Chinese Traditional and Herbal Drugs, 2010, 40(8): 1274-1277.

[9] Xu S Y, Bian R L, Chen X, Experimental Methodology of Pharmacology [M]. 3$^{rd}$ Edition, People's Medical Publishing House, Beijing, 2005.

[10] Cai W M, Zhang B B, Weng H L et al., Comparison study of eight markers of hepatic fibrosis serum [J]. Chinese Journal of Hepatology, 2004, 12(4): 219.

[11] Chen L Y, Dynamic effect of ShuGanRuanJian Decoction on NAG of hepatic fibrosis rats [J]. Journal of Shanxi College of Traditional Chinese Medicine, 2003, 4(3): 13-14.

[12] Wang G S, Han Z W, Effect of glycyrrhiza flavonoids on liver damage caused by ethanol [J]. Acta Pharmacologica Sinica, 1993, 9(4): 271-274.

[13] Zhou C Y, Ai L Y, Wang M, et al., Experimental study of Eucommia polysaccharide for anti hepatic fibrosis [J]. Chinese Traditional and Herbal Drugs, 2011, 42(2): 324-329.

What we claimed is:

1. A method for the treatment of a disease related to hepatic fibrosis in a subject in need thereof, the method comprising administering to said subject an effective amount of a composition comprising an aqueous extract of Radix Salviae Miltiorrhizae, wherein the disease is selected from the group consisting of liver cirrhosis, hepatitis, and liver cancer.

2. The method according to claim 1, wherein said composition is in a form selected from the group consisting of a tablet, a capsule and a dripping pill.

3. The method according to claim 2, wherein said composition is in the form of a dripping pill.

4. The method according to claim 1, wherein said treatment inhibits liver damage and reduces an increase of ALT, AST level in serum caused by liver cell damage.

5. The method according to claim 1, wherein said treatment includes protection of liver function and increasing synthesis of TP and ALB when liver function is damaged.

6. The method according to claim 1, wherein said treatment inhibits activation proliferation of liver stellate cells and reduces α-SMA expression in liver tissue.

7. The method according to claim 1, wherein said treatment increases activity of SOD in liver tissue and reduces MDA expression, so as to inhibit activation of liver stellate cells.

8. The method according to claim 1, wherein said treatment inhibits overdeposition of extracellular matrix of liver cells and increase of collagen, reducing content of type IV collagen in serum and reduces Hyp level in liver tissue.

9. The method according to claim 1, wherein said treatment inhibits damage of liver function, increases NAG level in serum and promotes collagen decomposition in extracellular matrix of liver cells.

* * * * *